(12) United States Patent
Luo et al.

(10) Patent No.: US 12,374,133 B2
(45) Date of Patent: Jul. 29, 2025

(54) DOMAIN-SPECIFIC HUMAN-MODEL COLLABORATIVE ANNOTATION TOOL

(71) Applicant: Huawei Cloud Computing Technologies Co., Ltd., Gui'an New District (CN)

(72) Inventors: Rui Luo, Bellevue, WA (US); Jiebo Luo, Pittsford, NY (US); Lin Chen, Seattle, WA (US)

(73) Assignee: Huawei Cloud Computing Technologies Co., Ltd., Guizhou (CN)

( * ) Notice: Subject to any disclaimer, the term of this patent is extended or adjusted under 35 U.S.C. 154(b) by 420 days.

(21) Appl. No.: 17/656,820

(22) Filed: Mar. 28, 2022

(65) Prior Publication Data

US 2022/0222952 A1 Jul. 14, 2022

Related U.S. Application Data

(63) Continuation of application No. PCT/US2019/056758, filed on Oct. 17, 2019.

(51) Int. Cl.
*G06V 20/70* (2022.01)
*G06N 20/00* (2019.01)
(Continued)

(52) U.S. Cl.
CPC .......... *G06V 20/70* (2022.01); *G06N 20/00* (2019.01); *G06V 10/751* (2022.01); *G06V 10/993* (2022.01)

(58) Field of Classification Search
CPC .......... G06N 20/00; G06T 2207/20081; G06T 2207/20084; G06T 2207/20092;
(Continued)

(56) References Cited

U.S. PATENT DOCUMENTS

2002/0194019 A1 12/2002 Evertsz
2009/0172036 A1 7/2009 Marx
(Continued)

FOREIGN PATENT DOCUMENTS

CN 106796621 A 5/2017
WO WO-2021076139 A1 4/2021

OTHER PUBLICATIONS

"International Application Serial No. PCT/US2019/056758, International Preliminary Report on Patentability mailed Apr. 28, 2022", 7 pgs.
(Continued)

*Primary Examiner* — Manuchehr Rahmjoo
(74) *Attorney, Agent, or Firm* — Schwegman Lundberg & Woessner, P.A.

(57) ABSTRACT

A human-model collaborative annotation system for training human annotators includes a database that stores images previously annotated by an expert human annotator and/or a machine learning annotator, a display that displays images selected from the database, an annotation system that enables human annotators to annotate images presented on the display, and an annotation training system. The annotation training system selects an image sample from the database for annotation by a human annotator, receives one or more proposed annotations from the annotation system, compares the human annotator's one or more proposed annotations to previous annotations of the image sample by the expert human annotator or machine learning annotator, presents attention maps on the display to draw the human annotator's attention to any annotation errors identified by the comparing, and selects a next training image sample from the database based on any errors identified in the comparing step.

20 Claims, 11 Drawing Sheets

(51) Int. Cl.
*G06V 10/75* (2022.01)
*G06V 10/98* (2022.01)

(58) Field of Classification Search
CPC ....... G06T 7/0012; G06T 7/10; G06V 10/751; G06V 10/993; G06V 20/70; G16H 30/40; G16H 50/20
See application file for complete search history.

(56) References Cited

U.S. PATENT DOCUMENTS

| | | |
|---|---|---|
| 2012/0070811 A1 | 3/2012 | Fox et al. |
| 2015/0086133 A1 | 3/2015 | Grady et al. |
| 2015/0089337 A1 | 3/2015 | Grady et al. |
| 2018/0268737 A1 | 9/2018 | Garnavi et al. |
| 2019/0034596 A1 | 1/2019 | Hartmann et al. |
| 2020/0033615 A1* | 1/2020 | Kim .................... G03H 1/08 |
| 2020/0134858 A1* | 4/2020 | Yang .................... G06T 7/0004 |
| 2023/0138380 A1* | 5/2023 | Chen .................... G06F 18/2148 |
| | | 382/131 |

OTHER PUBLICATIONS

"International Application Serial No. PCT/US2019/056758, International Search Report mailed Jul. 13, 2020", 5 pgs.

"International Application Serial No. PCT/US2019/056758, Written Opinion mailed Jul. 13, 2020", 5 pgs.

Aodha, Oisin Mac, et.al., "Teaching Categories to Human Learners with Visual Explanations", IEEE/CVF Conference on Computer Vision and Pattern Recognition, (Jun. 18, 2018), 3820-3828.

"Chinese Application No. 201980101444.5, First Office Action dated Oct. 25, 2024", (Oct. 25, 2024), 9 pgs.

Esses, Steven J., et al., "Automated image quality evaluation of T2-weighted liver MRI utilizing deep learning architecture", J Magn Reson Imaging. Mar. 2018;47(3):723-728. doi: 10.1002/jmri. 25779. Epub Jun. 3, 2017. PMID: 28577329, (Mar. 2018), 723-728.

* cited by examiner

DOMAIN-SPECIFIC HUMAN-MODEL COLLABORATIVE ANNOTATION TOOL

CROSS-REFERENCE TO RELATED APPLICATIONS

This application is a continuation of International Application No. PCT/US2019/056758, filed on Oct. 17, 2019, entitled "DOMAIN-SPECIFIC HUMAN-MODEL COLLABORATIVE ANNOTATION TOOL," the benefit of priority of which is claimed herein, and which application is hereby incorporated herein by reference in its entirety.

TECHNICAL FIELD

This application is related to annotation tools and, in particular, to domain-specific human-model collaborative annotation tools that train human annotators and machine learning systems to improve the efficiency of the domain-specific image labeling process.

BACKGROUND

In the medical imaging domain, deep learning is widely used to solve classification, detection, and segmentation problems. Labeled (annotated) data is critical for training a deep learning model. However, the medical image data type varies based on the type of imaging device used and the anatomy/tissue being examined, which increases the difficult of labeling such domain-specific data.

Domain-specific image annotation requires annotators with professional training and domain knowledge. The experience level of the annotator largely affects the annotation quality. Unfortunately, the extreme shortage in experienced annotators for labeling diverse biomedical data has created problems in providing efficient evaluation and treatments.

Currently, there are several generic labelling tools used to label images. One group of labelling tools uses hand drawn annotation. For example, the LabelIMG tool supports bounding boxes and one-class tagging. The VGG Image annotator has the option of adding objects and image attributes or tags. Other labelling tools, such as Supervise.ly and Labelbox, use models to provide semantic segmentation and to help predict the label for model training with human confirmation. Other labelling tools use active learning or reinforcement learning to train models using a few labeled images. The active learning models select uncertain examples and solicit help from human reviewers to complete the labelling. To produce more accurate predictions, machine learning models are used in systems such as AWS SageMaker Ground Truth and Huawei Cloud ModelArts. Such systems provide annotation tools that choose images to show human annotators and use the newly labeled images for further training of the machine learning model. The Polygon RNN++ segmentation tool sequentially produces vertices of the polygon outlining an object. This allows a human annotator to interfere at any time and to correct a vertex, as needed, to produce a more accurate segmentation.

Unfortunately, such prior art systems generally do nothing to solve the shortage of domain experts for annotation.

SUMMARY

Various examples are now described to introduce a selection of concepts in a simplified form that are further described below in the Detailed Description. The Summary is not intended to identify key or essential features of the claimed subject matter, nor is it intended to be used to limit the scope of the claimed subject matter.

An end-to-end domain-specific human-model collaborative annotation system and method is described that trains human annotators to improve the efficiency of the domain-specific image labeling process to address the shortage of human domain experts. The human-model collaborative annotation system described herein transfers expert knowledge to the new human annotator through a personalized training process while simultaneously providing additional samples for training a machine learning system. In sample embodiments, the human-model collaborative annotation system includes at least the following features:

1. An annotation system that includes an annotator training system that provides image samples for inexperienced annotators to label. The sampling and training process is personalized and is based on the annotators' mistakes. Attention maps are used to teach annotators to learn from their mistakes.

2. An evaluation stage within the annotator training system grades the annotators and provides reliable personalized feedback to the annotators in response to their submitted annotations.

3. By integrating learned domain knowledge and general human intelligence, newly trained annotators may contribute labels to help enlarge the pool of labeled samples and to improve the annotation system training model.

According to a first aspect of the present disclosure, there is provided a training method for training human annotators to annotate images. The training method includes presenting an image sample to a human annotator for annotation, wherein the image sample has been previously annotated by at least one of an expert human annotator and a machine learning annotator; receiving one or more proposed annotations from the human annotator; comparing the human annotator's one or more proposed annotations to previous annotations of the image sample by the expert human annotator or machine learning annotator; presenting attention maps to draw the human annotator's attention to an annotation error identified by the comparing; and selecting a next image sample based on any errors identified in the comparing.

According to a second aspect of the present disclosure, there is provided a human-model collaborative annotation system that includes a database that stores images previously annotated by at least one of an expert human annotator and a machine learning annotator; a display that displays images selected from the database; an annotation system adapted to enable a human annotator to annotate images presented on the display; and an annotation training system. The annotation training system selects an image sample from the database for display on the display for annotation by the human annotator, receives one or more proposed annotations from the annotation system, compares the human annotator's one or more proposed annotations to previous annotations of the image sample by the expert human annotator or machine learning annotator, presents attention maps on the display to draw the human annotator's attention to any annotation errors identified by the comparing, and selects a next image sample from the database based on any errors identified in the comparing.

According to a third aspect of the present disclosure, there is provided a non-transitory computer-readable medium storing computer instructions for training human annotators to annotate images, that when executed by one or more processors, cause the one or more processors to perform operations comprising: presenting an image sample to a human annotator for annotation, wherein the image sample has been previously annotated by at least one of an expert human annotator and a machine learning annotator; receiving one or more proposed annotations from the human annotator; comparing the human annotator's one or more proposed annotations to previous annotations of the image sample by the expert human annotator or machine learning annotator; presenting attention maps to draw the human annotator's attention to an annotation error identified by the comparing; and selecting a next image sample based on any errors identified in the comparing.

In a first implementation of any of the preceding aspects, the human annotator's annotation performance is evaluated by applying a weighting function and numeric metrics to comparison results from comparing the human annotator's one or more proposed annotations to previous annotations of the image sample by the expert human annotator or machine learning annotator.

In a second implementation of any of the preceding aspects, image samples are presented for annotation by the human annotator once the human annotator has been evaluated to have an annotation performance above a threshold and annotated image samples from the human annotator are contributed to a pool of image samples including image samples previously annotated by the expert human annotator or machine learning annotator.

In a third implementation of any of the preceding aspects, the annotated image samples from the human annotator contributed to the pool include a weighting based on the annotation performance of the human annotator.

In a fourth implementation of any of the preceding aspects, the human annotator is certified for future annotation tasks when the human annotator's annotation performance is above a predetermined level for annotations of a type for which the human annotator has been trained.

In a fifth implementation of any of the preceding aspects, the annotation performances for multiple human annotators for a same group of images are compared to establish a quality metric for the multiple human annotators.

In a sixth implementation of any of the preceding aspects, the attention maps are presented to a display with a personalized explanation of the annotation error.

In a seventh implementation of any of the preceding aspects, the images to be annotated include medical images, geographic images, and/or industry images.

The method may be performed and the instructions on the computer readable media may be processed by a system to train annotators, such as medical imaging annotators, and further features of the method and instructions on the computer readable media result from the functionality of the system. Also, the explanations provided for each aspect and its implementation apply equally to the other aspects and the corresponding implementations. The different embodiments may be implemented in hardware, software, or any combination thereof. Also, any one of the foregoing examples may be combined with any one or more of the other foregoing examples to create a new embodiment within the scope of the present disclosure.

BRIEF DESCRIPTION OF THE DRAWINGS

In the drawings, which are not necessarily drawn to scale, like numerals may describe similar components in different views. The drawings illustrate generally, by way of example, but not by way of limitation, various embodiments discussed in the present document.

DETAILED DESCRIPTION

Figure 1C:
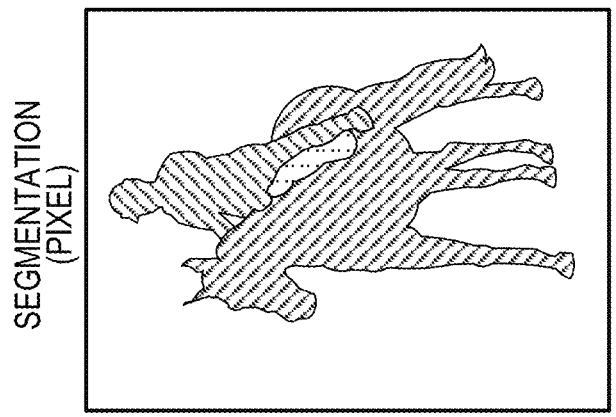
FIGS. 1A-1C illustrate images showing different types of image annotation including classification (FIG. 1A), detection (FIG. 1B), and segmentation (FIG. 1C).

It should be understood at the outset that although an illustrative implementation of one or more embodiments are provided below, the disclosed systems and/or methods described with respect to FIGS. 1-5 may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

The functions or algorithms described herein may be implemented in software in one embodiment. The software may include computer executable instructions stored on computer readable media or computer readable storage device such as one or more non-transitory memories or other type of hardware-based storage devices, either local or networked. Further, such functions may correspond to modules, which may be software, hardware, firmware or any combination thereof. Multiple functions may be performed in one or more modules as desired, and the embodiments described are merely examples. The software may be executed on a digital signal processor, ASIC, microprocessor, or other type of processor operating on a computer system, such as a personal computer, server or other computer system, turning such computer system into a specifically programmed machine.

Conventional annotation tools of the type mentioned above typically limit the interaction between a human and an annotation model to labelling (annotating) of images. For some tools, only simple explanations of the labels are provided. For domain-specific labeling tasks, the conventional annotation tools, such as those noted above, do nothing to remove the barriers for an annotator, particularly an inexperienced annotator. Such systems provide no knowledge transfer and no teaching or evaluation function. Generally, conventional annotation tools do nothing to address the shortage of domain experts for annotation through training of human annotators or by improving machine learning models.

The human-model collaborative annotation system described herein uses human experts and machine learning models to train non-expert human annotators while the human experts simultaneously train the machine learning models. An automated teaching system teaches the non-expert annotators using a comparison function and attention maps to draw the non-expert annotators' attention to any annotation errors. The teaching system is personalized to the annotator and contains an interactive learning element that contains the comparison function that lists and compares positive versus negative samples, or samples with different labels for annotators to recognize the differences. The teaching system also leverages the attention maps from the trained model to highlight the signals for given labels to teach annotators. The annotator may zoom in/out and select examples to view based on where the annotator is making mistakes to get the annotator up to speed faster. The teaching system also includes a comprehensive annotator evaluation system that may be used to guide the training, to certify the annotator, and to weight the annotator's contribution, once trained, to a database of annotated images. The teaching system further explains the reasoning behind the labels along with the attention maps to enhance the training.

In sample embodiments, the annotation system provides a service that provides a ground truth collection process where, for a given biomedical image labeling task, a machine learning model may be trained based on the samples labeled by experts with domain knowledge. The ground truth collection process is complemented by a personalized teaching process that teaches inexperienced annotators with little domain knowledge on the fly to understand how to label the images, thereby transferring the experts' knowledge to new annotators. Evaluation of the annotators' performance is also provided to generate an objective evaluation score. The evaluation score may then be used to further train the new annotators and to further refine the machine learning model using the newly labeled data subject to weighting factors. The training system determines what sample to show next based on the annotator's error and uses the attention maps to highlight the annotation error. For example, the next sample may be an image of the same type with similar attention maps. The samples would have the same type of area of attention for annotating the image.

Figure 1B:
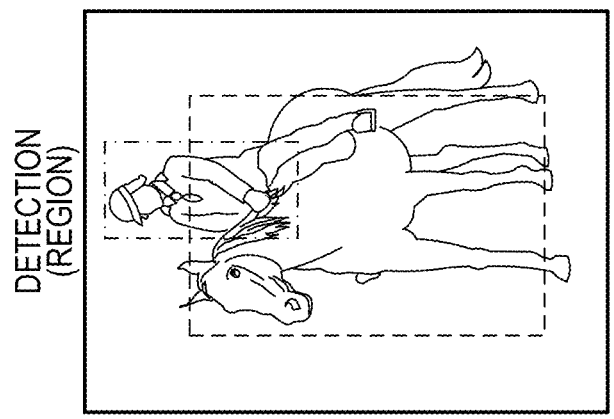
Figure 1A:
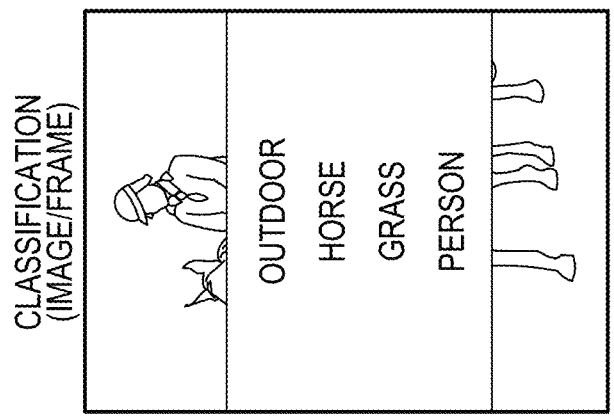

The image annotation described herein may be of different forms and applied to different types of images. FIGS. 1A-1C illustrate the three main types of image annotation including classification (FIG. 1A), detection (FIG. 1B), and segmentation (FIG. 1C). Image level annotation is used for classification. In this type of annotation, an image is given a label (e.g., brain tumor) if the image contains the label in its content. By way of example, FIG. 1A illustrates classifications of "outdoor," "horse," "grass," and "person" for an image containing each of these elements. Bounding box annotation as illustrated in FIG. 1B may be used for detection. In this type of annotation, a rectangle is drawn to closely enclose an object in an image. The rectangle usually contains an object of interest such as "person," "horse," or "tumor region." Contour annotation for segmentation is illustrated in FIG. 1C. In this type of annotation, a polygon is drawn surrounding the contour of an object to outline the object in the image corresponding to the labels. The polygon usually contains the area of interest such as "person," "horse," or "tumor." In each case, the object is matched to the label. The system and method described herein supports all three types of annotations.

Figure 2:
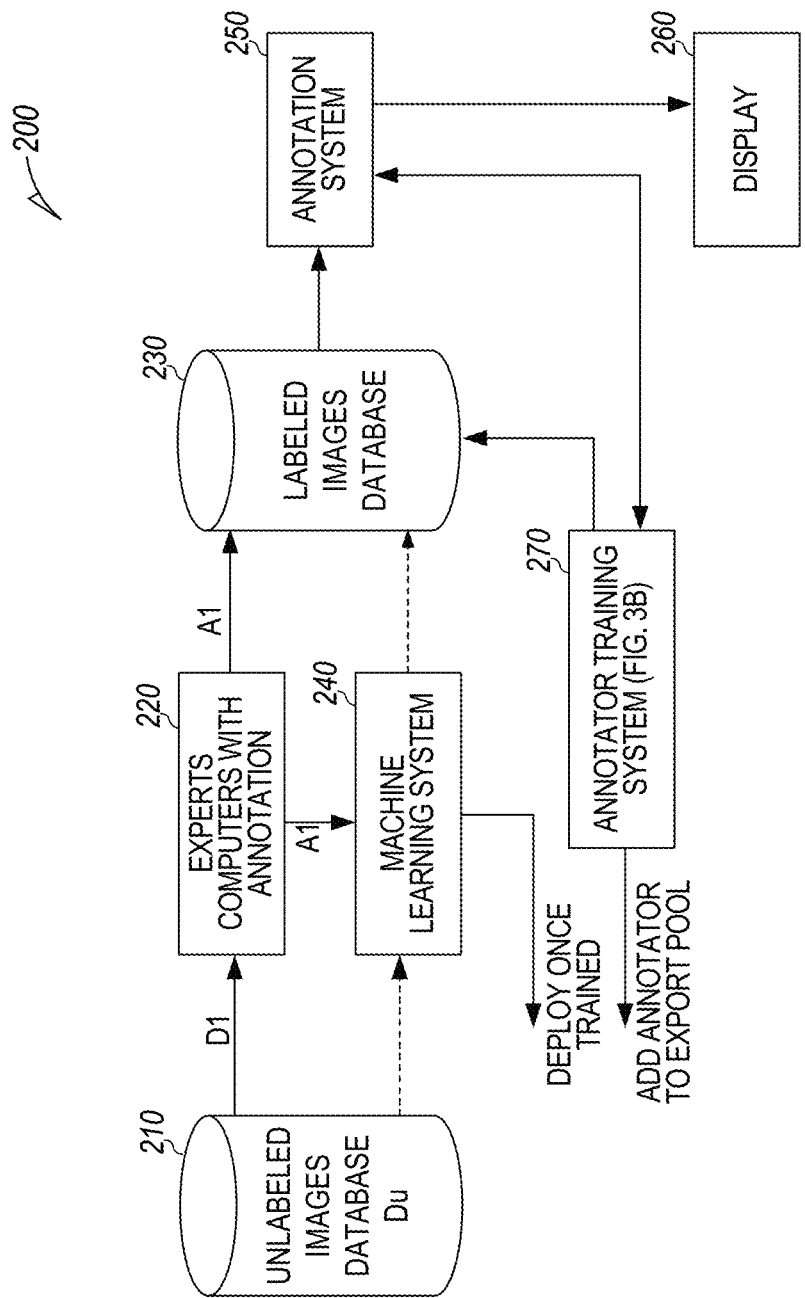
FIG. 2 illustrates a block diagram of a sample embodiment of a human-model collaborative annotation system.

FIG. 2 illustrates a block diagram of a sample embodiment of a human-model collaborative annotation system 200. In the system 200, unlabeled image data (D1) from a database 210 is provided to experts for labeling using the experts' computer system with annotation software 220. The resulting images labeled by the experts (A1) are provided to a labeled images database 230 to create a database of annotated images. The labeled images are also used to train a machine learning model of a machine learning system 240 that once trained may, in turn, receive unlabeled images from the database 210 and generate more annotated images for storage in the labeled images database 230. Also, once trained, the collaboratively trained machine learning model of the machine learning system 240 may be deployed for use by non-expert annotators.

In sample embodiments, the system 200 further includes an annotation system 250 that selects samples for presentation to non-expert human annotators on display 260 for labeling. In the sample embodiments, the non-expert human annotators may receive feedback from an annotator training system 270 that compares the annotated images generated by the non-expert human annotators using the annotation system 250 with the corresponding expert annotated images provided by the labeled image database 230. The feedback includes attention maps that teach the non-expert human annotators to learn from their mistakes. The evaluator's performance is evaluated, and the next image for annotation on the annotation system 250 by the non-expert human annotator is selected based on the performance of the non-expert human annotator in labeling a previously presented image. Once the non-expert human annotator receives consistently good ratings from the performance evaluation system, the non-expert human annotator may be added to the pool of expert annotators and permitted to annotate additional images that may be added to the pool of labeled samples in the labeled images database 230. The added images may be weighted with weightings based on the accuracy of the annotations by the non-expert human annotator, thus improving the training model.

In sample embodiments, the annotation for classification may be captured by the annotator inputting a label in a text box or checking a yes or no button for a given label. The annotation for a classification rectangle may be captured by the annotator dragging a mouse from top-left to right-bottom. The annotation for segmentation may be captured by clicking the vertexes of a polygon. The comparison may be done by comparing the annotator's proposed label Z with the ground truth label G where G and Z are labels for classification, a rectangle for detection, and a contour/polygon for segmentation.

The performance scores are calculated by comparing the ground truth label G and annotator label Z and averaging on all the images annotated by the annotator. For classification, it is correct only if Z equals G. For detection and segmentation, Intersection over Union (IOU) is used, which is calculated by the intersection area of Z and G divided by the union area of Z and G. The annotation is correct only if IOU is larger than a predefined threshold such as 0.5. The performance score is then used to weight the annotator annotation if the annotator's performance score passes a pre-defined threshold, such as 99%.

Figure 3A:
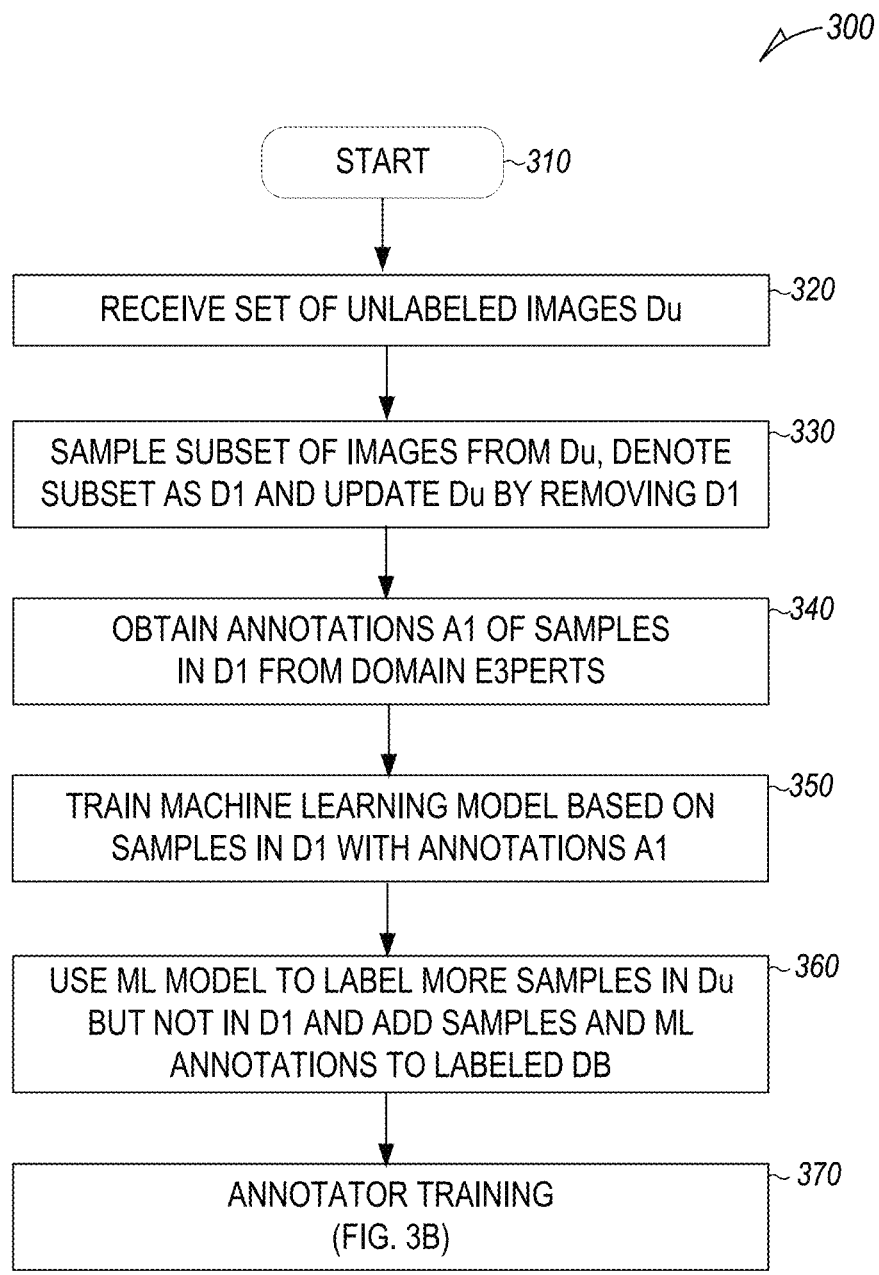
FIG. 3A illustrates a flow chart of a method for generating annotated images for annotator training in a sample embodiment.

FIG. 3A illustrates a flow chart of a method 300 for generating annotated images for annotator training in a sample embodiment. The method 300 starts at 310 and receives a set of unlabeled images $D_u$ from the unlabeled images database 210 at 320. A subset of images from $D_u$ are sampled at 330. The sampled subset is denoted as D1, and $D_u$ is updated by removing D1. The sampled subset D1 is provided to the annotation systems 220 of domain expert annotators at 340 so that the expert annotators may annotate the samples in D1. The resulting annotations A1 are provided to the labeled images database 230. The expert annotations A1 of sample images in D1 also may be used to train a machine learning model of the machine learning system 240 at 350. The machine learning (ML) model also may be used at 360 to label more examples in $D_u$ but not in D1. The annotated samples in $D_u$ generated by the machine learning model may be added to labeled images database 230 along with the machine learning model labeled annotations. The labeled images in the labeled images database 230 are then ready for use by the annotator training system 270 at 370. The operation of the annotator training system 270 will be described below with respect to FIG. 3B.

As noted above, the annotator training system 270 teaches the new annotators the domain knowledge of the expert annotators. During a first iteration of teaching, the non-expert human annotators are provided with randomly selected samples from the labeled images database 230 to label and an automatic evaluation system evaluates the performance of the non-expert human annotators as described above. Based on the performance, the subsequent teaching process is personalized as follows:

1. Personalized sampling: More images are sampled that include the same types of features that caused mistakes by the non-expert human annotators during previous rounds of annotation and that may evidence some confusion. Unlike the active learning paradigm used in conventional annotation systems that only involves having the model select the most uncertain samples for annotators to label, the personalized annotation training system described herein addresses the confusion or uncertainty exhibited by the particular non-expert human annotator during the training process.

2. Personalized evaluation: The evaluation function compares the mistakes annotators make with the known labels and highlights the differences and areas using, for example, attention maps (as illustrated in FIG. 4) for annotators to learn (using generic human cognitive intelligence).

3. Personalized teaching: The system differentiates the learning process by selecting further samples based on each annotator's own cognitive intelligence and learning speed.

This makes the learning more effective and more engaging, which results in training the annotator more quickly and makes the annotation process more efficient.

Figure 3B:
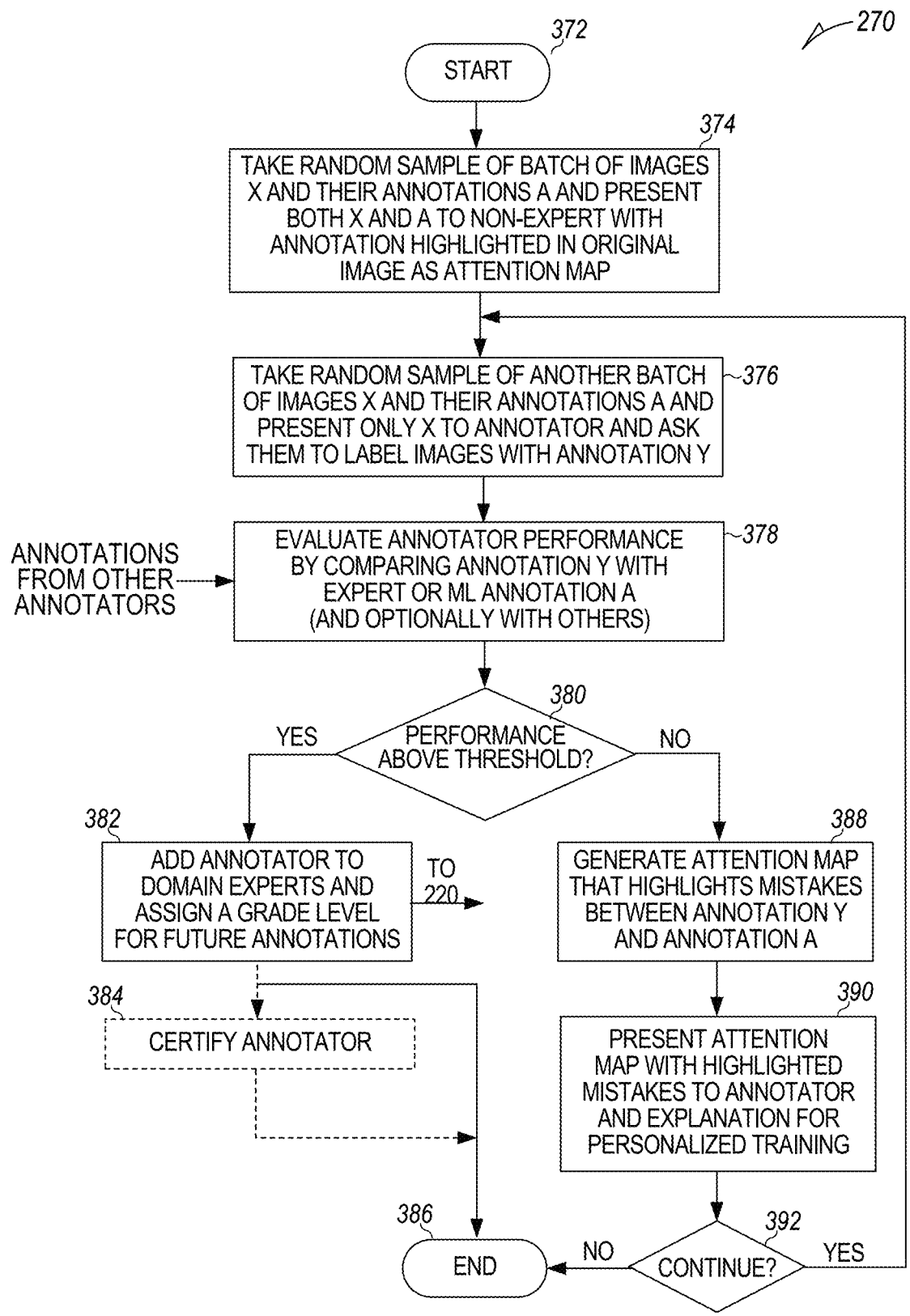
FIG. 3B illustrates a flow chart of operation of the annotator training system in a sample embodiment.

FIG. 3B illustrates a flow chart of operation of the annotator training system 270 in a sample embodiment. As illustrated, the method starts at 372 by taking a random sample of a batch of images X and their annotations A from labeled images database 230 and presenting both X and A to a non-expert human annotator with the annotation highlighted in the original image as an attention map at 374. A random sample of another batch of images X and their annotation A is taken at 376. Only the images X are presented to the non-expert human annotator asking the non-expert human annotator to label the images with the annotation Y. The annotation Y is evaluated at 378 to evaluate the performance of the non-expert human annotator by comparing annotator annotation Y with expert or machine learning model annotation A as described above. Optionally, at 378, the annotation Y may be compared with annotations from other annotators to assess annotation performances for multiple human annotators for a same group of images to establish a quality metric for the multiple human annotators.

It will be appreciated that evaluation is a key component to a teaching system, which should comprehensively analyze the performance of the annotators. In sample embodiments, the evaluation metrics may include, but are not limited to the accuracy of an annotator on each task and each label (e.g., detection and segmentation as well as intersection over union (IOU) that measures degree of overlap in images), the overall quality of an annotator's labels, and the learning curve (including history of speed and accuracy) of an annotator.

After the annotator's performance is evaluated at 378, the method checks at 380 to determine whether the annotator's performance is above a pre-defined threshold. If so, then the annotator may be added at 382 to the domain of experts that provide expert annotations at 220 in FIG. 2. However, the annotator is also assigned a grade level that may be used to weight their future annotations. For example, the future annotations may be adjusted by a weighting of between 0-1 depending upon the annotator's performance during the annotation training. Optionally, the annotator training system 270 may certify the annotator at 384 based on a predetermined certification process designed to provide an objective measure of an "expert" annotator. The annotator training process then ends at 386.

On the other hand, when the annotator's performance is below the pre-defined threshold at 380, training may continue. The further training includes generating at 388 an attention map that highlights the annotation mistakes from the comparison results of the annotator annotation Y and the expert or machine learning model annotation A. The attention map is presented to the annotator at 390 with highlighted mistakes and explanations of those mistakes to provide personalized training. The annotator training system 270 then determines at 392 whether the training is to continue. If not, the training ends at 386. However, if the training is to continue, the process returns to 376 to take another random sample of another batch of images and their annotations to repeat the process.

In sample embodiments, the annotation training system 270 also provides guidance as to what sample image to show next based on the error highlighted in one or more previous iterations of the training process. For example, in the case of image classification, the annotation training system 270 may present an image X to an annotator where the ground truth label for image X is known as Y but not shown to the annotator. The annotator makes a mistake by giving a label Z that is different from Y. The system generates an attention map with the area related to Y highlighted in X and showing the image X along with the highlighted attention map to guide the annotator. The annotation training system 270 then provides a sample of another image with the same label Y to reinforce the training with respect to the errors in identifying label Y. For detection and segmentation, the process is similar, and the differences are in the form of label Y, which is a rectangle for detection and a contour for segmentation. This process further enables personalized training by presenting images that emphasize the areas where the annotator is having difficulties. With such an evaluation system, the annotation training system 270 learns how to train the annotator in the next stage in a personalized way and how to integrate the annotator's labels with other labels, subject to a weighting factor. The annotation training system 270 may also certify an annotator for future tasks that require the same expertise.

Figure 3C:
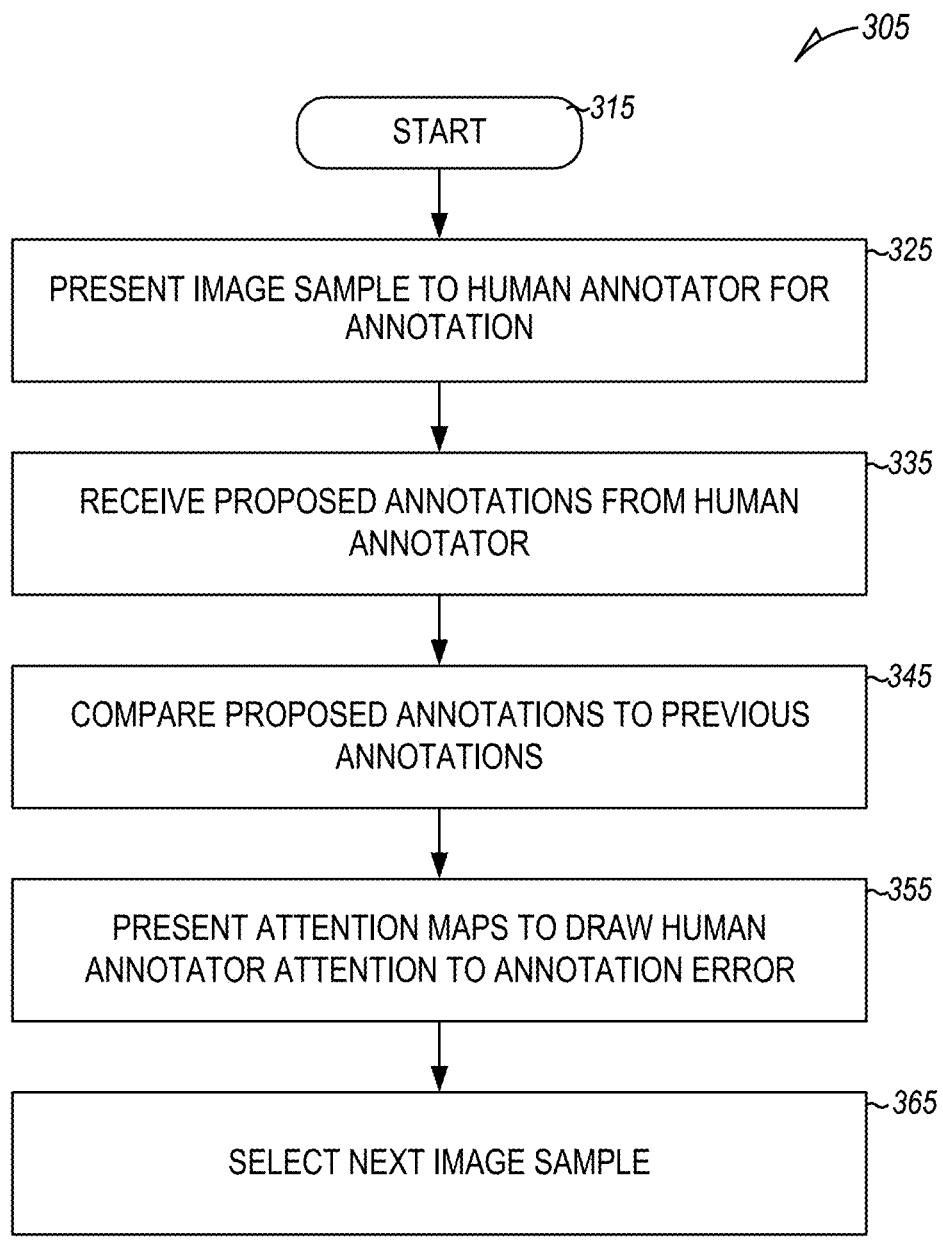
FIG. 3C illustrates a flow chart of operation of the annotator method in a sample embodiment.

FIG. 3C illustrates a flow chart of operation of the annotator method 305 in a sample embodiment. The method 305 starts at 315 and includes presenting 325 an image sample to a human annotator for annotation, wherein the image sample has been previously annotated by at least one of an expert human annotator and a machine learning annotator. Method 305 includes receiving 325 one or more proposed annotations from the human annotator. Method 305 includes comparing 345 the human annotator's one or more proposed annotations to previous annotations of the image sample by the expert human annotator or machine learning annotator. Method 305 includes presenting 355 attention maps to draw the human annotator's attention to an annotation error identified by the comparing. Method 305 includes selecting 365 a next image sample based on any errors identified in the comparing.

Figures 4A, 4B, 4C:
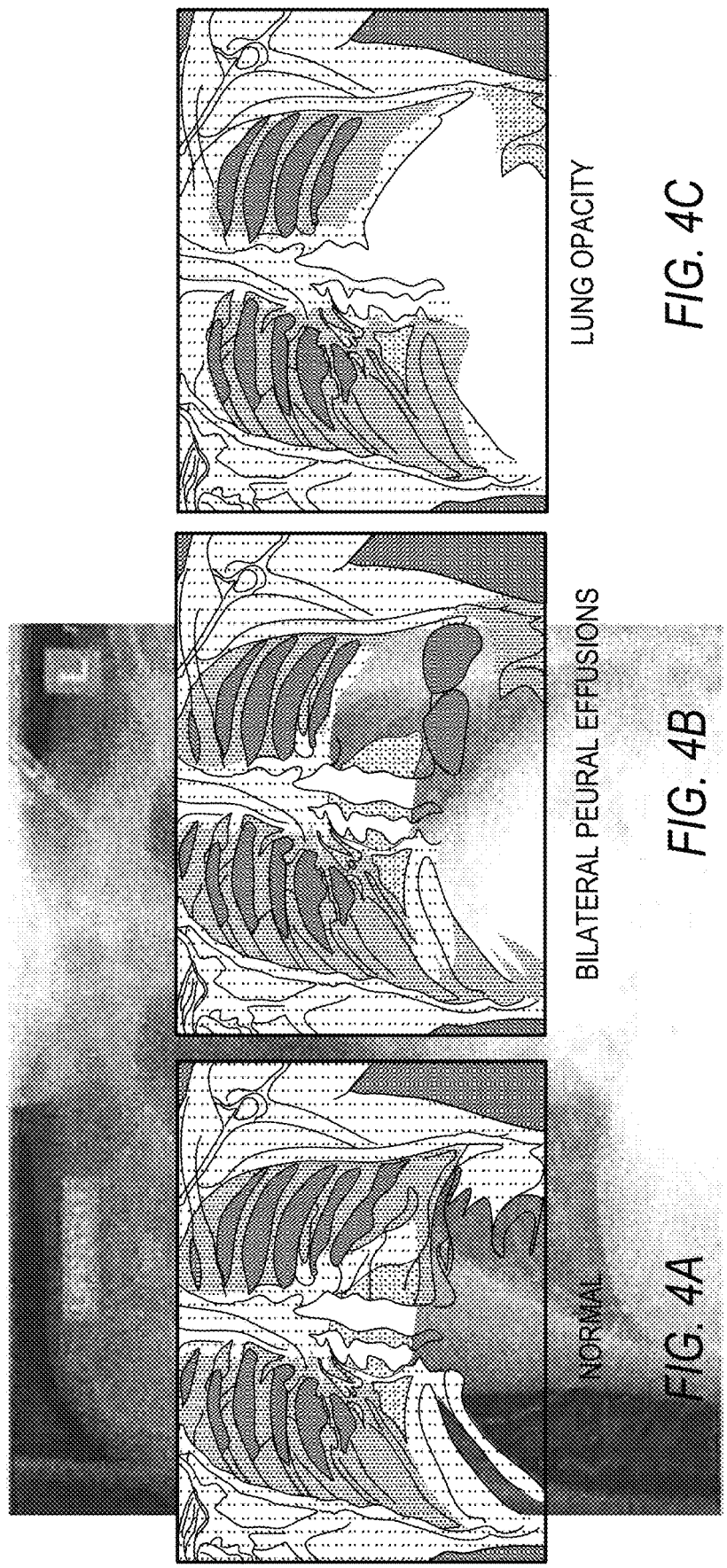
FIGS. 4A-4C illustrate sample images that have not been annotated, including an image of a normal lung (FIG. 4A), an image of a lung with bilateral pleural effusions (FIG. 4B), and an image of a lung with lung opacity (FIG. 4C).
Figure 4D:
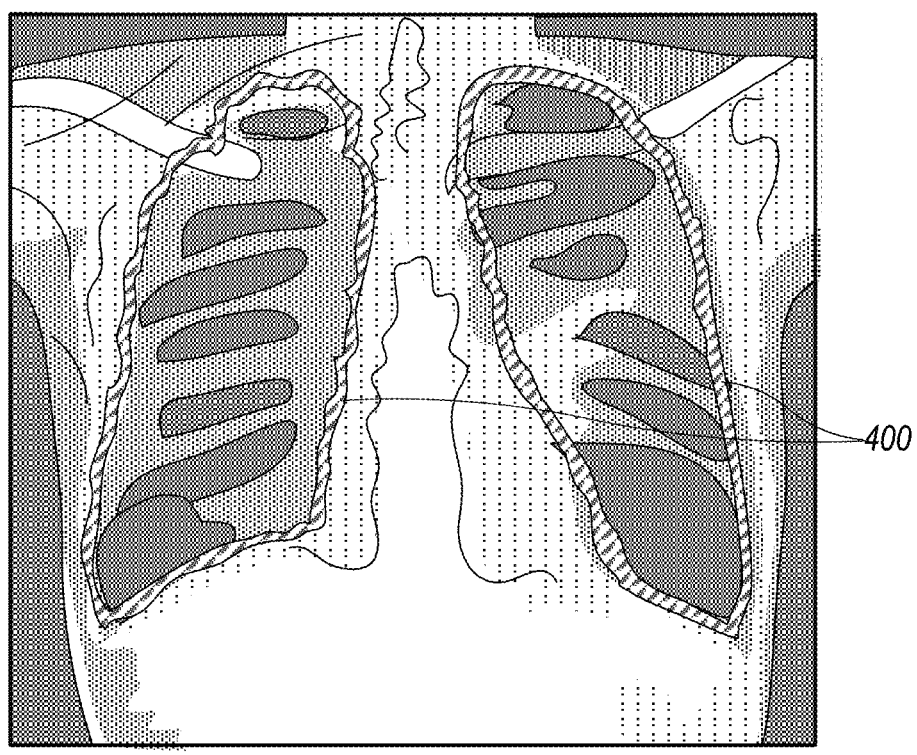
FIG. 4D illustrates a lung image that has been segmented.
Figure 4E:
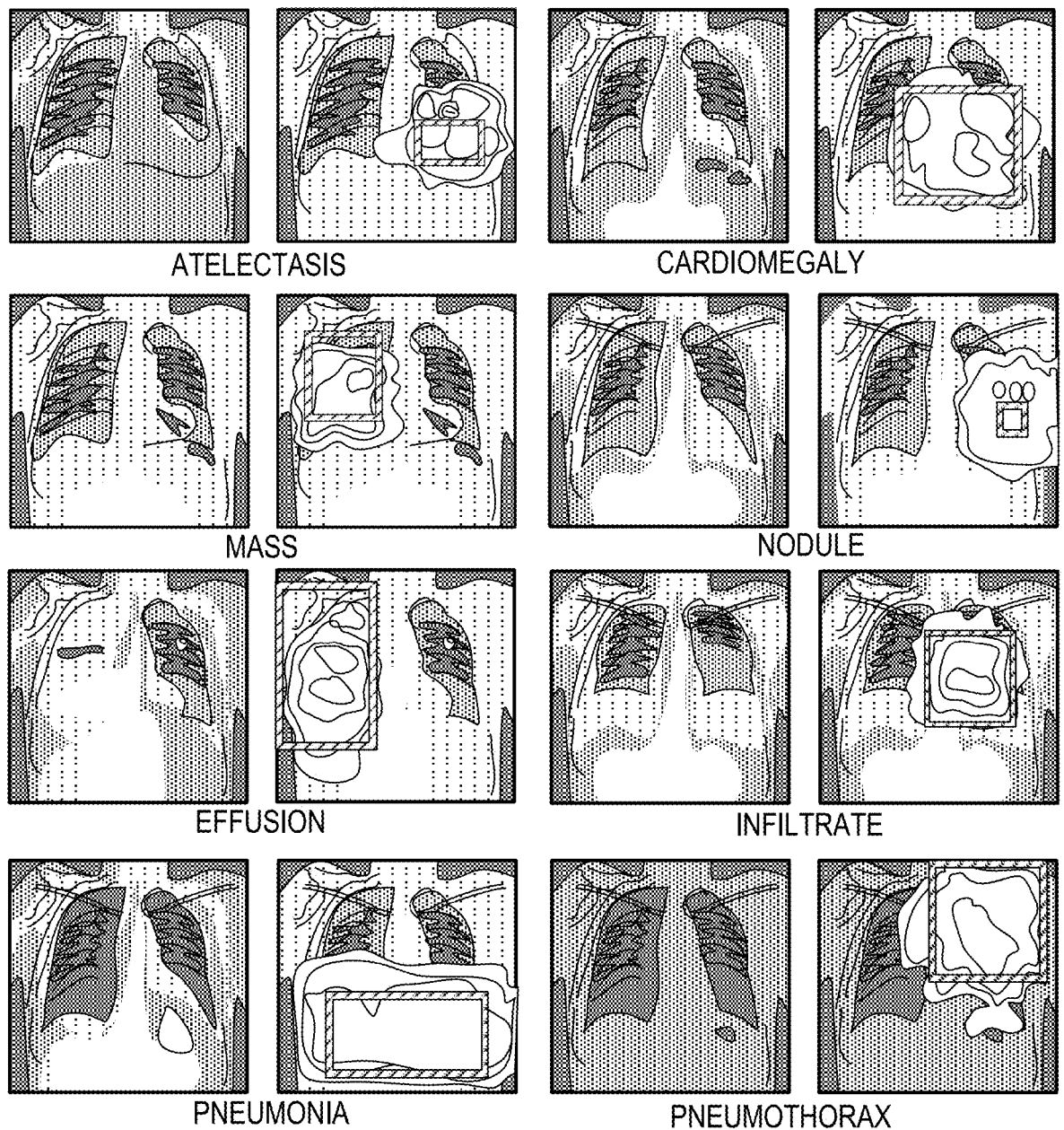
FIG. 4E illustrates lung images with boxes showing the ground truth annotations from domain experts for sample disease detection.
Figure 4F:
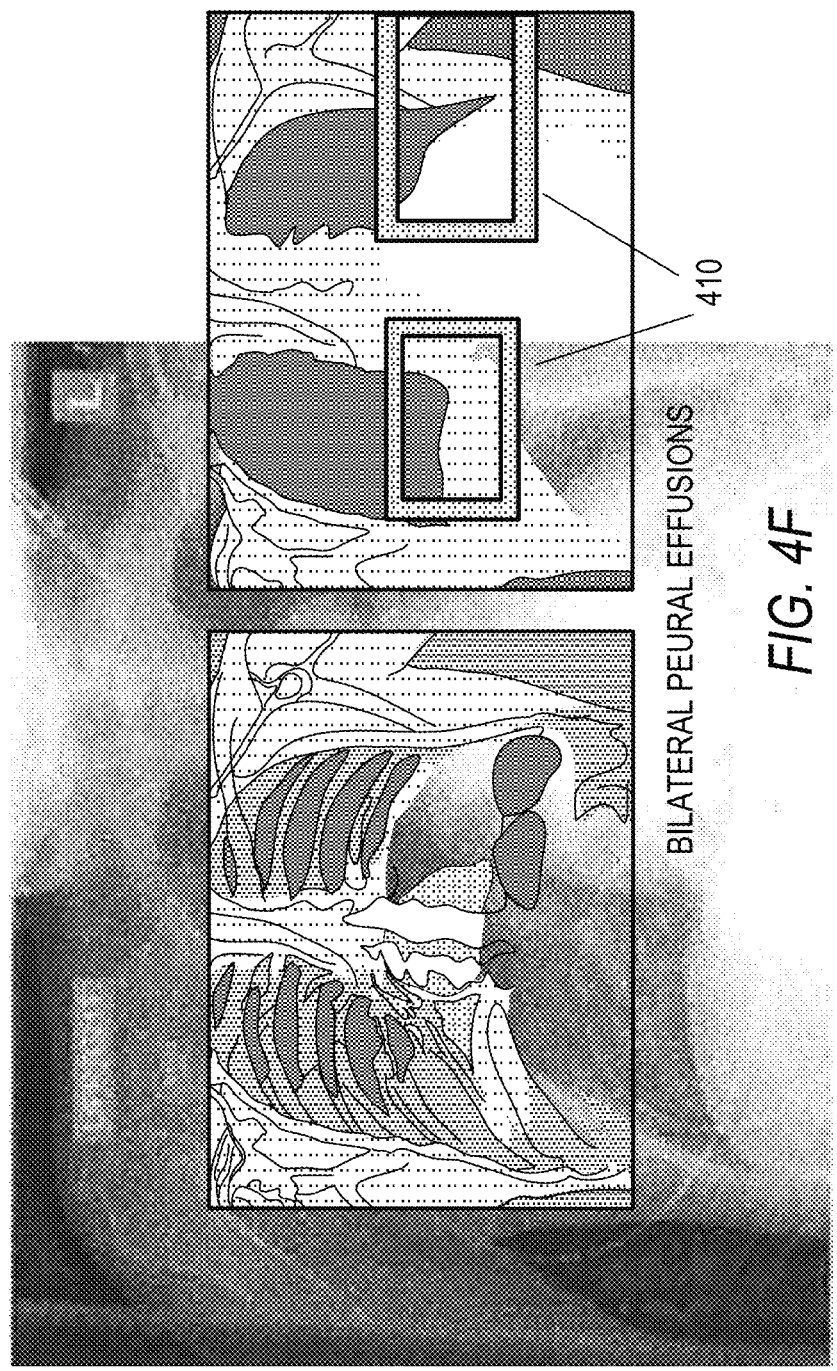
FIGS. 4F-4G illustrate machine-generated attention maps used to show the human annotators what was missed in the annotation process including bilateral pleural effusions (FIG. 4F) and lung opacity (FIG. 4G).
Figure 4G:
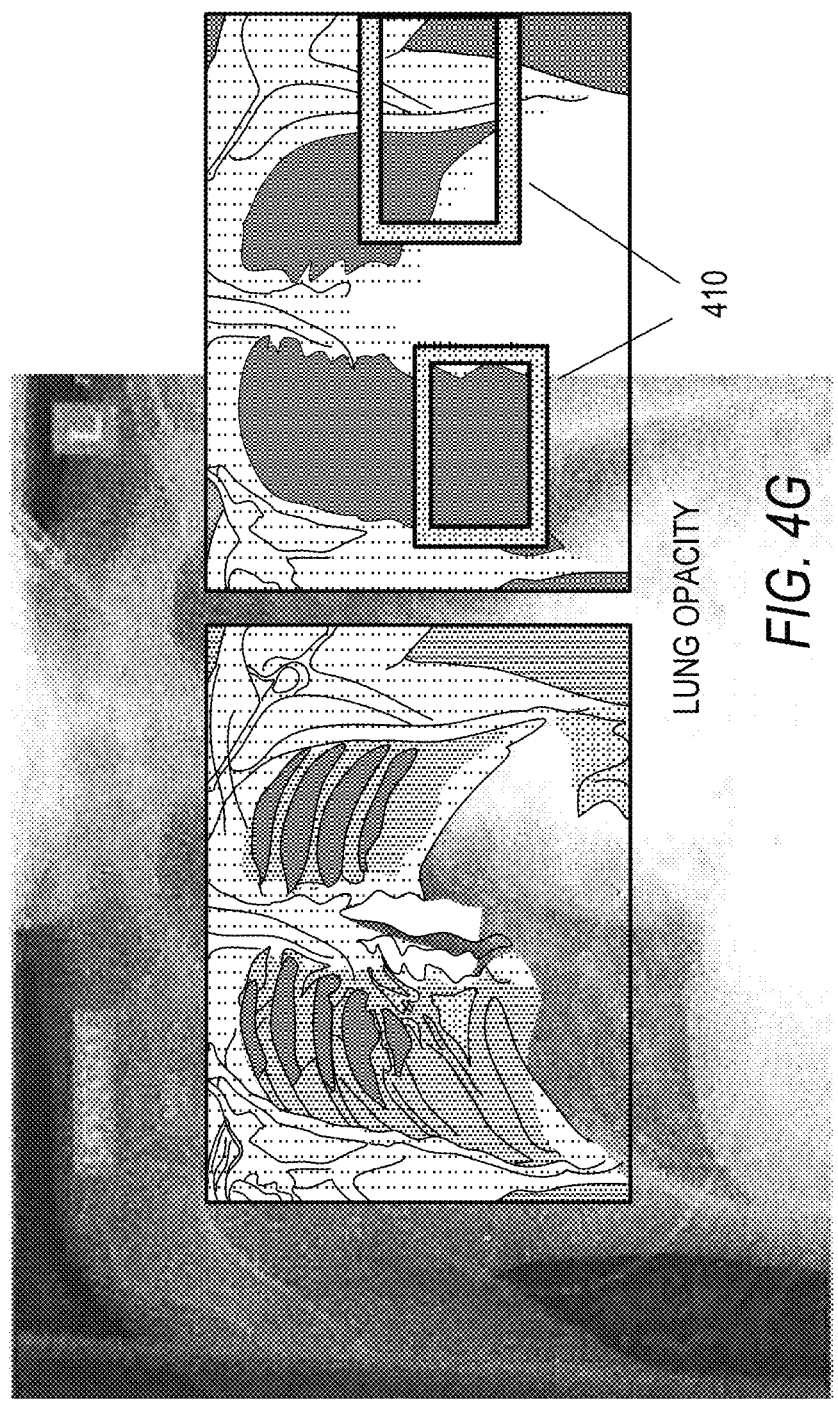

FIGS. 4A-4C illustrate sample images that have not been annotated, including an image of a normal lung (FIG. 4A), an image of a lung with bilateral pleural effusions (FIG. 4B), and an image of a lung with lung opacity (FIG. 4C). FIG. 4D illustrates a lung image that has been segmented at 400. FIG. 4E illustrates lung images with boxes showing the ground truth annotations from domain experts for sample disease detection. FIGS. 4F-4G illustrate machine-generated attention maps used to show the human annotators what was missed in the annotation process including bilateral pleural effusions (FIG. 4F) and lung opacity (FIG. 4G). Such attention maps draw the annotator's attention to the areas of interest with emphasis on the errors made by the annotator. In sample embodiments, the attention maps may also be presented with an explanation of the correct annotation and/or the erroneous annotation for improved training.

In sample embodiments, the attention map uses a different color or intensity value at 410 to highlight the area to guide the user to the correct area for correcting the annotation. The attention map may include the following features:

The image is given the label because of the highlighted area;

The annotator makes a mistake in the highlighted read.

There are many methods used in the art to obtain such attention maps. For example, given an input image to a well-trained machine learning model, such as a deep neural network, the machine learning model outputs a label with a ground truth that matches exactly the annotations from the domain expert. This process is called forward pass from an input image to an output prediction. By replacing the output prediction with the ground truth and running the process backward, the input image may be recovered with the area that related to the ground truth highlighted. The machine-generated attention map is thus used to show the human annotators what was missed in the annotation process.

The teaching component and human-model collaborative annotation system described herein offers several advantages over conventional annotation systems. For example, the human-model collaborative annotation system described herein may alleviate or solve the shortage of expert annotators. The human-model collaborative annotation system also removes or lowers the barrier for domain-specific annotation tasks via knowledge transfer between machine intelligence and human intelligence (both expert intelligence and generic human cognitive intelligence), including annotation for medical images, geographic images, and industry images. Also, trained annotators may be certified for future annotation tasks that require the same or similar expertise. Even if not fully certified, the trained annotator also may create new training images with weighted annotations for use by the training system.

The evaluation system also may be used to evaluate the labeling quality for crowd workers. By comparing the annotations with each other, the human-model collaborative annotation system may help to integrate labels from different workers at different times and places.

It will be further appreciated that the human-model collaborative annotation system may utilize a machine learning model and a deep learning algorithm to transfer domain expert knowledge to other people. Beside its usage in annotation as described herein, the human-model collaborative annotation system described herein also may be used in education and in industrial professional training.

Figure 5:
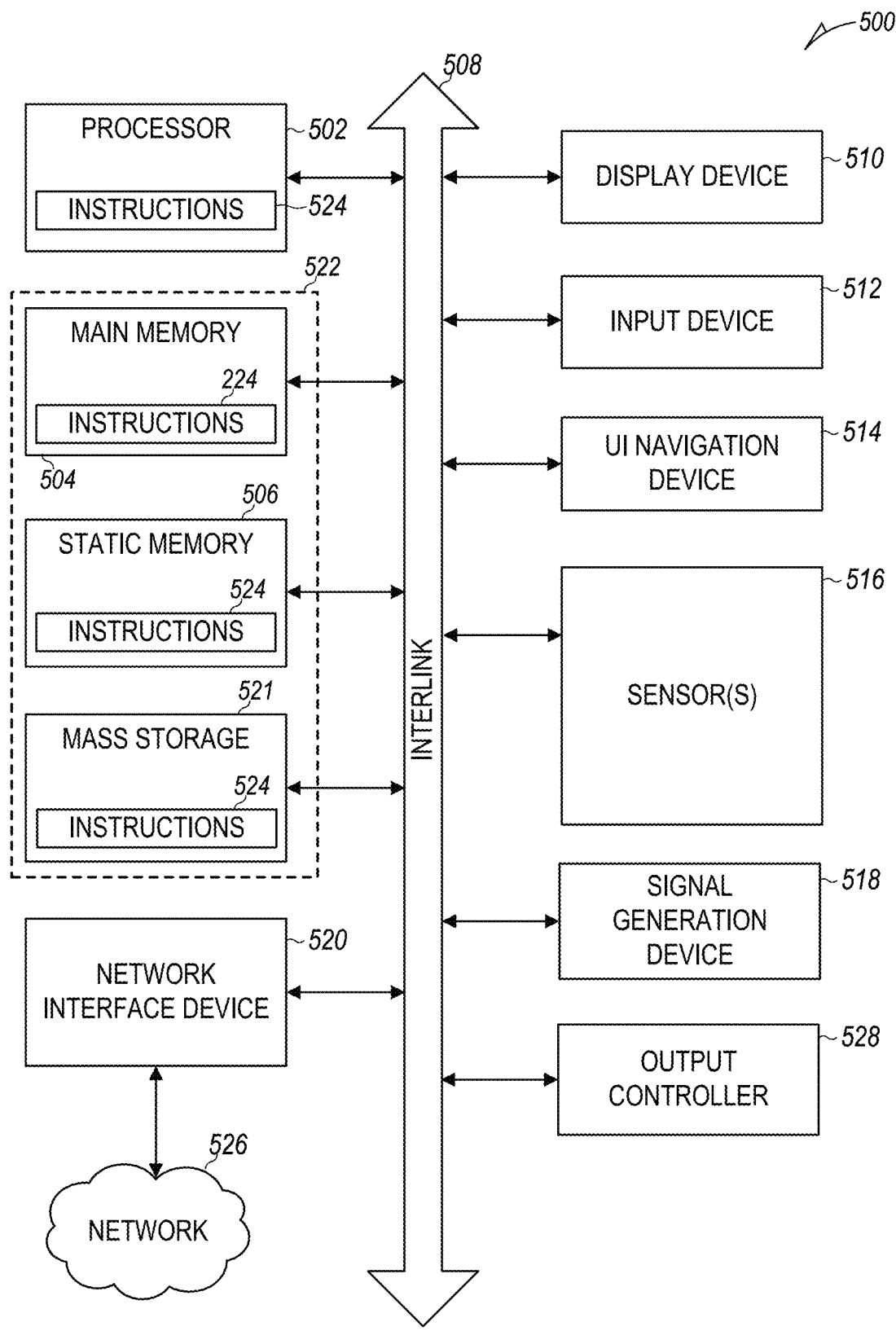
FIG. 5 illustrates a block diagram of circuitry for performing the methods according to sample embodiments.

FIG. 5 illustrates a block diagram of an example machine 500, such as an annotation training system, upon which any one or more of the techniques (e.g., methodologies) discussed herein may perform. In alternative embodiments, the machine 500 may operate as a standalone device or may be connected (e.g., networked) to other machines. In a networked deployment, the machine 500 may operate in the capacity of a server machine, a client machine, or both in server-client network environments. In an example, the machine 500 may act as a peer machine in a peer-to-peer (P2P) (or other distributed) network environment. The machine 500 may be a personal computer (PC), a tablet PC, a set-top box (STB), a personal digital assistant (PDA), a mobile telephone, a web appliance, an IoT device, automotive system, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic, components, devices, packages, or mechanisms. Circuitry is a collection (e.g., set) of circuits implemented in tangible entities that include hardware (e.g., simple circuits, gates, logic, etc.). Circuitry membership may be flexible over time and underlying hardware variability. Circuitries include members that may, alone or in combination, perform specific tasks when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable participating hardware (e.g., the execution units or a loading mechanism) to create members of the circuitry in hardware via the variable connections to carry out portions of the specific tasks when in operation. Accordingly, the computer readable medium is communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time.

The machine (e.g., computer system) 500 (e.g., the annotation system 250, the annotator training system 270, etc.) may include a hardware processor 502 (e.g., a CPU, a graphics processing unit (GPU), a hardware processor core, or any combination thereof, etc.), a main memory 504 and a static memory 506, some or all of which may communicate with each other via an interlink (e.g., bus) 508. The machine 500 may further include a display device 510, an alphanumeric input device 512 (e.g., a keyboard), and a user interface (UI) navigation device 514 (e.g., a mouse). In an example, the display unit 510, input device 512, and UI navigation device 514 may be a touch screen display. The machine 500 may additionally include a signal generation device 518 (e.g., a speaker), a network interface device 520, and one or more sensors 516, such as a global positioning system (GPS) sensor, compass, accelerometer, or other sensor. The machine 500 may include an output controller 528, such as a serial (e.g., USB, parallel, or other wired or wireless (e.g., infrared (IR), near field communication (NFC), etc.) connection to communicate or control one or more peripheral devices (e.g., a printer, card reader, etc.).

The machine 500 may include a machine readable medium 522 on which is stored one or more sets of data structures or instructions 524 (e.g., software) embodying or utilized by any one or more of the techniques or functions described herein. The instructions 524 may also reside, completely or at least partially, within the main memory 504, within static memory 506, or within the hardware processor 502 during execution thereof by the machine 500. In an example, one or any combination of the hardware processor 502, the main memory 504, or the static memory 506 may constitute the machine readable medium 522.

While the machine readable medium 522 is illustrated as a single medium, the term "machine readable medium" may include a single medium or multiple media (e.g., a centralized or distributed database, or associated caches and servers) configured to store the one or more instructions 524.

The term "machine readable medium" may include any medium capable of storing or encoding instructions for execution by the machine 500 and that cause the machine 500 to perform any one or more of the techniques of the present disclosure, or capable of storing, encoding or carrying data structures used by or associated with such instructions. Non-limiting machine-readable medium examples include solid-state memories, and optical and magnetic media. In an example, a massed machine-readable medium comprises a machine-readable medium with multiple particles having invariant (e.g., resting) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 524 (e.g., software, programs, an operating system (OS), etc.) or other data are stored on the storage device 521, may be accessed by the memory 504 for use by the processor 502. The memory 504 (e.g., DRAM) is typically fast, but volatile, and thus a different type of storage than the storage device 521 (e.g., an SSD), which is suitable for long-term storage, including while in an "off" condition, may be used. The instructions 524 or data in use by a user or the machine 500 are typically loaded in the memory 504 for use by the processor 502. When the memory 504 is full, virtual space from the storage device 521 may be allocated to supplement the memory 504; however, because the storage device 521 device is typically slower than the memory 504, and write speeds are typically at least twice as slow as read speeds, use of virtual memory may greatly reduce user experience due to storage device latency (in contrast to the memory 504, e.g., DRAM). Further, use of the storage device 521 for virtual memory may greatly reduce the usable lifespan of the storage device 521.

In contrast to virtual memory, virtual memory compression (e.g., the Linux® kernel feature "ZRAM") uses part of the memory as compressed block storage to avoid paging to the storage device 521. Paging takes place in the compressed block until it is necessary to write such data to the storage device 521. Virtual memory compression increases the usable size of memory 504, while reducing wear on the storage device 521.

The instructions 524 may further be transmitted or received over a communications network 526 using a transmission medium via the network interface device 520 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, P2P networks, among others. In an example, the network interface device 520 may include one or more physical jacks (e.g., Ethernet, coaxial, or phone jacks) or one or more antennas to connect to the communications network 526. In an example, the network interface device 520 may include multiple antennas to wirelessly communicate using at least one of single-input multiple-output (SIMO), multiple-input multiple-output (MIMO), or multiple-input single-output (MISO) techniques.

The term "transmission medium" shall be taken to include any intangible medium capable of storing, encoding or carrying instructions for execution by the machine 500, and includes digital or analog communications signals or other intangible medium to facilitate communication of such software.

The above detailed description includes references to the accompanying drawings, which form a part of the detailed description. The drawings show, by way of illustration, specific embodiments in which the systems and methods described herein may be practiced. These embodiments are also referred to herein as "examples". Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" may include "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, i.e., a system, device, article, or process that includes elements in addition to those listed after such a term in a claim are still deemed to fall within the scope of that claim. Moreover, in the following claims, the terms "first," "second," and "third," and so forth, are used merely as labels, and are not intended to impose numerical requirements on their objects.

In various examples, the components, controllers, processors, units, engines, or tables described herein may include, among other things, physical circuitry or firmware stored on a physical device. As used herein, "processor" means any type of computational circuit such as, but not limited to, a microprocessor, a microcontroller, a graphics processor, a digital signal processor (DSP), or any other type of processor or processing circuit, including a group of processors or multi-core devices.

It will be understood that when an element is referred to as being "on," "connected to," or "coupled with" another element, it may be directly on, connected, or coupled with the other element or intervening elements may be present. In contrast, when an element is referred to as being "directly on," "directly connected to," or "directly coupled with" another element, there are no intervening elements or layers present. If two elements are shown in the drawings with a line connecting them, the two elements may be either be coupled, or directly coupled, unless otherwise indicated.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, the code may be tangibly stored on one or more volatile or non-volatile tangible computer-readable media, such as during execution or at other times. Examples of these tangible computer-readable media may include, but are not limited to, hard disks, removable magnetic disks, removable optical disks (e.g., CDs and DVDs), magnetic cassettes, memory cards or sticks, RAMs, ROMs, SSDs, UFS devices, eMMC devices, and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

What is claimed is:

1. A method for training human labelers to label images, the method comprising:
   receiving, by one or more processors, a set of domain-specific images;
   presenting, by the one or more processors, an image sample from the set of domain-specific images on a display to a human labeler for labeling via a graphical user interface, wherein the image sample has been previously labeled by at least one of an expert human and labeler or a machine learning model trained on expert-labeled images;
   receiving, by one or more processors, one or more proposed labels from the human labeler through the graphical user interface;
   comparing, by the one or more processors, the one or more proposed labels to previous labels of the image sample by the expert human labeler or machine learning model;
   generating, by the one or more processors, computer-generated attention maps comprising a visual overlay superimposed on the image sample, wherein the computer-generated attention maps identify specific region containing a labeling error identified by the comparing;
   presenting, by the one or more processors, the computer-generated attention maps on the display with the visual overlay and a personalized explanation of the labeling error to guide the human labeler in correcting the labeling error;
   evaluating, by the one or more processors, a labeling performance of the human labeler based on the comparing using a weighting function and numeric metrics; and
   selecting, by the one or more processors, a next image sample based on types of errors identified in the comparing, wherein the next image sample contains similar labeling challenges to reinforce training in areas where errors were identified.

2. The method of claim 1, further comprising evaluating, by one or more processors, a labeling performance of the human labeler based on the comparing using a weighting function and numeric metrics.

3. The method of claim 2, further comprising presenting, by one or more processors, image samples on the display for labeling by the human labeler once the labeling performance is above a threshold and contributing labeled image samples from the human labeler to a pool of image samples including image samples previously labeled by the expert human labeler or machine learning model.

4. The method of claim 3, wherein the labeled image samples from the human labeler contributed to the pool include a weighting based on the labeling performance of the human labeler.

5. The method of claim 1, further comprising certifying, by one or more processors, the human labeler for future labeling tasks when an labeling performance of the human labeler is above a predetermined level for labels of a type for which the human labeler has been trained.

6. The method of claim 1, further comprising comparing, by one or more processors, labeling performances for multiple human labelers for a same group of images to establish a quality metric for the multiple human labelers.

7. The method of claim 1, wherein presenting the computer-generated attention maps on the display to draw a human labeler attention to the labeling error identified by the comparing includes providing a personalized explanation of the labeling error on a display with the computer-generated attention maps.

8. The method of claim 1, wherein the images to be labeled comprise at least one of medical images, geographic images, and industry images.

9. A human-model collaborative labeling system, comprising:
- a database that stores images previously labeled by at least one of an expert human labeler and a machine learning model trained on expert-labeled images;
- a display that displays images selected from the database;
- a labeling system adapted to enable a human labeler to label images presented on the display; and
- a labeling training system including one or more processors that:
  - selects an image sample from the database for display on the display for labeling by the human, labeler through a graphical user interface;
  - receives one or more proposed labels from the labeling system;
  - compares the one or more proposed labels to previous labels of the image sample by the expert human labeler or machine learning, model;
  - generates computer-generated attention maps comprising a visual overlay on the display to draw a human labeler attention to a specific region containing a labeling error identified by the comparing;
  - presents, by the one or more processors, the computer-generated attention maps on the display with the visual overlay and a personalized explanation of the labeling error to guide the human labeler in correcting the labeling error;
  - evaluates, by the one or more processors, a labeling performance of the human labeler based on the comparing using a weighting function and numeric metrics; and
  - selects a next image sample from the database based on any errors identified in the comparing;
- wherein the computer-generated attention maps include a computer-generated visual overlay superimposed on the image sample, and wherein the next image sample contains similar labeling challenges to reinforce training in areas where errors were identified.

10. The system of claim 9, wherein the labeling training system further evaluates an labeling performance of the human labeler by applying a weighting function and numeric metrics to comparison results from comparing the one or more proposed labels to previous labels of the image sample by the expert human labeler or machine learning model.

11. The system of claim 10, wherein the labeling training system further presents image samples for labeling by the human labeler once the human labeler has been evaluated to have an labeling performance above a threshold and contributes labeled image samples from the human labeler to the database.

12. The system of claim 11, wherein the labeled image samples from the human labeler contributed to the database include a weighting based on the labeling performance of the human labeler.

13. The system of claim 9, wherein the labeling training system further certifies the human labeler for future labeling tasks when an labeling performance of the human labeler is above a predetermined level for labeling s of a type for which the human labeler has been trained.

14. The system of claim 9, wherein the labeling training system further compares labeling performances for multiple human labelers for a same group of images to establish a quality metric for the multiple human labelers.

15. The system of claim 9, wherein the labeling training system provides a personalized explanation of the labeling error on the display with the computer-generated attention maps.

16. The system of claim 9, wherein the images to be labeled comprise at least one of medical images, geographic images, and industry images.

17. A non-transitory computer-readable medium storing computer instructions for training human labelers to label images, that when executed by one or more processors, cause the one or more processors to perform operations comprising:
- receiving, by one or more processors, a set of domain-specific images;
- presenting, by the one or more processors, an image sample from the set of domain-specific images on a display to a human labeler for labeling via a graphical user interface, wherein the image sample has been previously labeled by at least one of an expert human and labeler or a machine learning model trained on expert-labeled images;
- receiving, by the one or more processors, one or more proposed labels from the human labeler via the graphical user interface;
- comparing the one or more proposed labels to previous labels of the image sample by the expert human labeler or machine learning model;
- generating computer-generated attention maps comprising visual overlay superimposed on the image sample, wherein the computer-generated attention maps identify specific region containing a labeling error identified by the comparing;
- presenting the computer-generated attention maps on the display with the visual overlay and a personalized explanation of the labeling error to guide the human labeler in correcting the labeling error;
- evaluating a labeling performance of the human labeler based on the comparing using a weighting function and numeric metrics; and
- selecting a next image sample from the set based on types of errors identified in the comparing, wherein the next image sample contains similar labeling challenges to reinforce training in areas where errors were identified.

18. The medium of claim 17, further comprising instructions that when executed by the one or more processors cause the one or more processors to evaluate an labeling performance of the human labeler based on the comparing using a weighting function and numeric metrics.

19. The medium of claim 18, further comprising instructions that when executed by the one or more processors cause the one or more processors to present image samples for labeling by the human labeler once the human labeler has been evaluated to have the labeling performance above a threshold and to contribute labeled image samples from the human labeler to a pool of image samples including image samples previously labeled by the expert human labeler or machine learning model.

20. The medium of claim 19, wherein the labeled image samples from the human labeler contributed to the pool include a weighting based on the labeling performance of the human labeler.

* * * * *

UNITED STATES PATENT AND TRADEMARK OFFICE
CERTIFICATE OF CORRECTION

PATENT NO. : 12,374,133 B2  
APPLICATION NO. : 17/656820  
DATED : July 29, 2025  
INVENTOR(S) : Luo et al.

Page 1 of 1

It is certified that error appears in the above-identified patent and that said Letters Patent is hereby corrected as shown below:

On the Title Page

In item (73), in "Assignee", in Column 1, Line 2, delete "Guizhou" and insert --Gui'an New District-- therefor In the Claims In Column 14, Line 14, in Claim 1, before "labeler", delete "and"

In Column 15, Line 19, in Claim 9, delete "human," and insert --human-- therefor In Column 15, Line 25, in Claim 9, delete "learning," and insert --learning-- therefor Signed and Sealed this  
Twenty-eighth Day of October, 2025

John A. Squires  
*Director of the United States Patent and Trademark Office*